(12) United States Patent  
Berg

(10) Patent No.: US 6,367,085 B1  
(45) Date of Patent: Apr. 9, 2002

(54) HEAD SUSPENSION FOR AN AIR SUPPLIED HOOD SYSTEM

(75) Inventor: Richard C. Berg, Bloomington, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/216,995

(22) Filed: Dec. 21, 1998

(51) Int. Cl.$^7$ ................................................. A42B 1/00
(52) U.S. Cl. .......................... 2/202; 2/9; 2/416; 2/452; 2/DIG. 11; 128/201.24
(58) Field of Search .................... 2/8, 9, 11, 416, 2/420, 452, 202, 205, 206, DIG. 11, 15; 128/201.22, 201.24, 201.29; 351/155, 156

(56) References Cited

U.S. PATENT DOCUMENTS

| | | | | |
|---|---|---|---|---|
| 2,135,397 A | * | 11/1938 | Jackson | 2/8 |
| 2,156,181 A | * | 4/1939 | Jackson | 2/8 |
| 2,169,745 A | * | 8/1939 | Shipman | 2/8 |
| 2,187,932 A | * | 1/1940 | Cornell | 2/8 |
| 2,758,307 A | * | 8/1956 | Treiber | 2/9 |
| 2,759,187 A | * | 8/1956 | Woodard | 2/8 |
| 2,760,197 A | * | 8/1956 | Jones | 2/8 |
| 4,040,123 A | | 8/1977 | Williams | 2/10 |
| 4,753,378 A | | 6/1988 | Kastendieck et al. | 224/181 |
| 4,888,831 A | | 12/1989 | Oleson | 2/420 |
| 4,986,282 A | | 1/1991 | Stackhouse et al. | 128/857 |
| 5,341,512 A | | 8/1994 | Noble | 2/6.2 |

OTHER PUBLICATIONS

Product Information: "Positive Pressure Respirators," Minnesota Mining and Manufacturing Company (3M), Dec., 1996.

* cited by examiner

Primary Examiner—Michael A. Neas
(74) Attorney, Agent, or Firm—Michaele A. Hakamaki

(57) ABSTRACT

A head suspension for use with a flexible hood is disclosed. The hood is used with supplied air sources in situations when a full face or half face respirator is inconvenient. The head suspension includes a headband that is preferably adjustable in circumference and a lens mount attached to the headband at the ends of the lens mount and with at least two braces. The braces are positioned to be non-parallel to each other. The lens of the hood is mounted from the lens mount. The brace provides added stability to the lens and hood.

17 Claims, 3 Drawing Sheets

HEAD SUSPENSION FOR AN AIR SUPPLIED HOOD SYSTEM

BACKGROUND

Supplied air hoods are used for respiratory protection and to keep the worker's face, head and hair free from contamination. They may also reduce the risk of skin absorption of chemicals. Many times, hoods are the only viable devices to provide protection for workers with beards, long sideburns, small faces, or other features that may increase the difficulty of achieving a proper seal with other types of respirators.

A hood covers the wearer's head and neck and drapes onto the shoulders. The portion that drapes onto the shoulders is called a shroud. An inner shroud, that is tucked into the wearer's shirt or garment, may also be provided. The hood itself does not provide head impact protection. Air is typically supplied to the interior of the hood at the front or back via a hose. Supplied air hoods are available from many manufacturers, for example, Minnesota Mining and Manufacturing Company, St. Paul, Minn. (hereinafter referred to as "3M"); E.D. Bullard Company, Cynthiana, Ky.; Dalloz Safety, Reading, Pa.; and North Safety Equipment, Cranston, R.I.

Hoods typically are made from a non-woven material having a polymeric coating on the surface; one example of such a commercially available material is TYVEC QCr™. Hoods can also be made from paper, polymeric film or cloth. Preferably, the hood material is impervious to air or liquid flow through the material.

A transparent plastic lens is attached to the hood material. The lens is designed to provide protection against splash hazards, as well provide the wearer with a field of vision. The lens also is designed to retain the supplied air within the hood.

A hood is generally used in combination with headgear, either a head suspension or a hardcap. The head suspension or hardcap is used to support the hood on the wearer's head and to provide at least a minimal space between the wearer's face and the plastic lens. The plastic lens is typically secured to an extending brim of the hardcap or to an extending shield or lens mount band on the head suspension. The hood is attached to the headgear typically in a detachable manner.

A hardcap is used with a hood when impact protection for the head is needed, for example, from overhead obstructions or potentially falling objects. A hardcap can be similar to a construction worker's hardhat.

In many work environments, the impact protection provided by the hardcap is not needed; thus a head suspension is used with the hood instead. A head suspension is basically a flexible frame that fits onto the wearer's head and includes an extended mount band that supports the hood and provides some distance between the lens and the wearer's face.

Wearers of hoods with head suspensions have encountered problems caused by the outer shroud. In some instances when a wearer turns his head, the hood does not move in conjunction with the head. Instead, the head turns and the hood does not follow because of the weight of the shroud holding the hood back, thereby impairing the wearer's side vision. In addition, the lens may collapse onto the wearer's face when the wearer attempts to turn his head.

SUMMARY OF THE INVENTION

In view of the above, there is a need for a head suspension design that securely fixes the position of the plastic lens in relation to the wearer's field of vision and prevents the lens from collapsing toward the wearer's face. This invention affords an improved head suspension with enhanced lens stability.

In one embodiment of the present invention, a head suspension, for use with a hood and for suspending a transparent lens therefrom is provided. The head suspension comprises a headband and a lens mount, the lens mount for mounting the lens to the head suspension. The lens mount is extended from the headband and is attached to the headband by at least two nonparallel braces that bridge the area from the headband to the lens mount. In a preferred embodiment, the lens mount is attached to the headband in at least four points via two braces and two mounting points.

The braces provide increased lateral support for the hood and lens and are positioned between the headband and the lens mount so that they are nonparallel to each other. Preferably, the braces are positioned at an angle less than 90° in relation to the headband so that the braces diverge as they extend from the headband to the lens mount. The braces may be individual pieces that are assembled together with the headband and lens mount. Alternatively, the braces may be formed integral with the headband or integral with the lens mount.

These and other advantages and features that characterize the invention are illustrated below in the detailed description and accompanying drawing.

DETAILED DESCRIPTION OF PREFERRED EMBODIMENTS

The head suspension and hood of the present invention will be described in relation to the accompanying drawings.

The head suspension of the present invention is usable with a variety of hoods, but in general with supplied air hoods. Supplied air hoods and head suspensions are available from many manufacturers, for example, Minnesota Mining and Manufacturing Company, St. Paul, Minn. (hereinafter referred to as "M"); E.D. Bullard Company, Cynthiana, Ky.; Dalloz Safety, Reading, Pa., and North Safety Equipment, Cranston, R.I.

Figure 1:
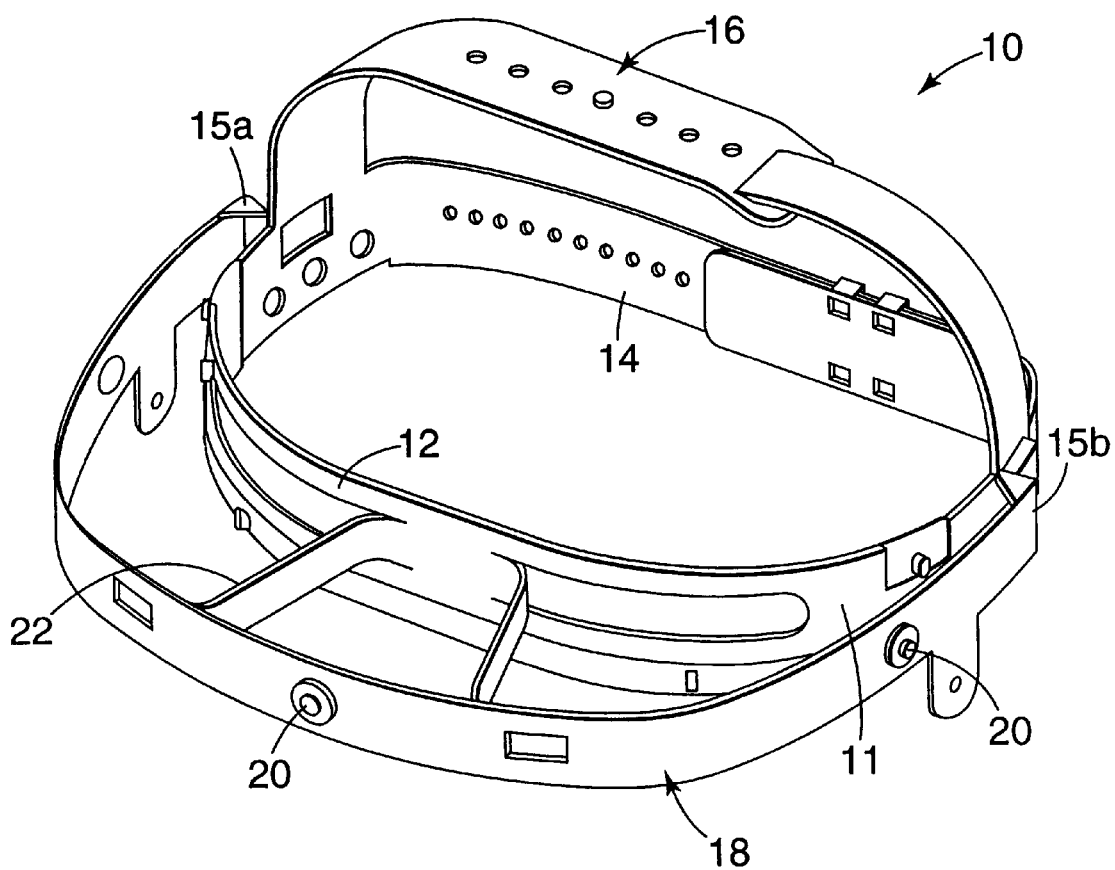
FIG. 1 is a perspective view of a hood head suspension 10 in accordance with one embodiment of the present invention.

Referring now to the Figures, wherein like numerals represent like parts throughout the several views, a preferred embodiment of the present invention will be described. In FIG. 1, there is shown a head suspension 10 for use with a hood (not shown). The head suspension 10 is secured on a wearer's head by headband 11 which comprises a forehead strap 12 and back strap 14. The headband 11 provides a frame that rests on the wearer's head. The head suspension 10 shown in FIG. 1 includes a headband 11 and a crown strap 16; the crown strap 16 improves the positioning and stability of the head suspension 10 on the wearer's head. Optionally, a chinstrap may be added to provide increased security on the wearer's head.

In some designs, the headband 11 may be a single unitary piece, that is, there may be no discernible break or transition from the forehead strap 12 to the back strap 14.

Alternatively, forehead strap 12 and back strap 14 may be multiple pieces joined to form headband 11. Similarly, crown strap 16 may be unitary with, for example, back strap 14, or crown strap 16 may be an individual piece joined to headband 11. Further, any of forehead strap 12, back strap 14 or crown strap 16 may comprises multiple pieces or sections.

The head suspension 10 is designed to be adjustable to fit a wide range of head sizes. Headband 11 can be adjustable, for example, by a quick snap-fit mechanism (such as used for baseball caps) incorporated into back strap 14. Alternatively, a ratcheting adjustment mechanism can be used. Both of these methods for adjusting the circumference of headbands are well known.

The inner surface of headband 11 may have a cushioning pad secured thereto to provide a soft cushioning effect on the wearer's head. A cushioning pad may also improve the fit of the headband on the wearer's head. An example of a cushioning pad is a low-density foam. Such a foam will compress to provide a secure and comfortable fit against the head, but will return to generally its original shape after it is removed from against the head. A sweatband or sweatpad may be used in conjunction with a cushioning pad or without.

Crown strap 16, such as shown in FIG. 1, can also be adjustable, for example by a quick snap-fit mechanism. By adjusting crown strap 16, the relative position of the wearer's head in the head suspension 10 is controlled. With such an adjusting feature, the wearer can raise the head suspension 10 higher so that the headband 11 or other part of the head suspension 10 does not pinch or rub the ears or other areas on the head.

One primary function of head suspension 10 is to secure the plastic lens (not shown). Attached to the headband 11 (i.e., the combination of the forehead strap 12 and back strap 14) is a lens mount 18. By attaching either the lens or hood to lens mount 18, a gap is provided between the lens and the wearer's face. This gap allows supplied air to circulate between the lens and the wearer's face. Lens mount 18 is generally positioned about 2 to 10 cm from forehead strap 12, preferably about 5 cm. Either the top of the lens or the hood is attached to the lens mount 18 by some method such as snaps, hooks, clips, or a hook and loop type system (often referred to as VELCRO™, although numerous other hook and loop systems are available from other sources). For purposes of this application, attaching the lens or hood to the lens mount shall be considered mounting the lens from the lens mount 18.

The lens mount 18 typically is an elongate horizontal piece, similar to a strap or band, and is attached to the headband 11 at each end of the lens mount 18 at mounting points 15a and 15b. It has been found that conventional head suspensions, where the lens mount is supported only at the end mounting points 15a and 15b, can be undesirable because of the low degree of stability provided to the lens in relation to the hood assembly. This instability is noticed, for example, when the wearer turns his head and the lens and lens mount do not follow the head. The head suspension 10 of the present invention has solved the problem of insufficient support and stability of the lens in the lateral direction. Additionally, head suspension 10 prevents the lens and lens mount from collapsing in toward the wearer.

According to the present invention, in addition to attaching the lens mount 18 to the headband 11 at the mounting points 15a and 15b at the ends of lens mount 18. The lens mount 18 is attached to headband 11 at least at two other points, preferably near the center of lens mount 18. The addition of braces 22 extending from lens mount 18 to the headband 11 (in particular to forehead strap 12) provides increased strength and stability to prevent the delay in lens movement and to prevent collapsing of the lens and lens mount.

Figure 3:
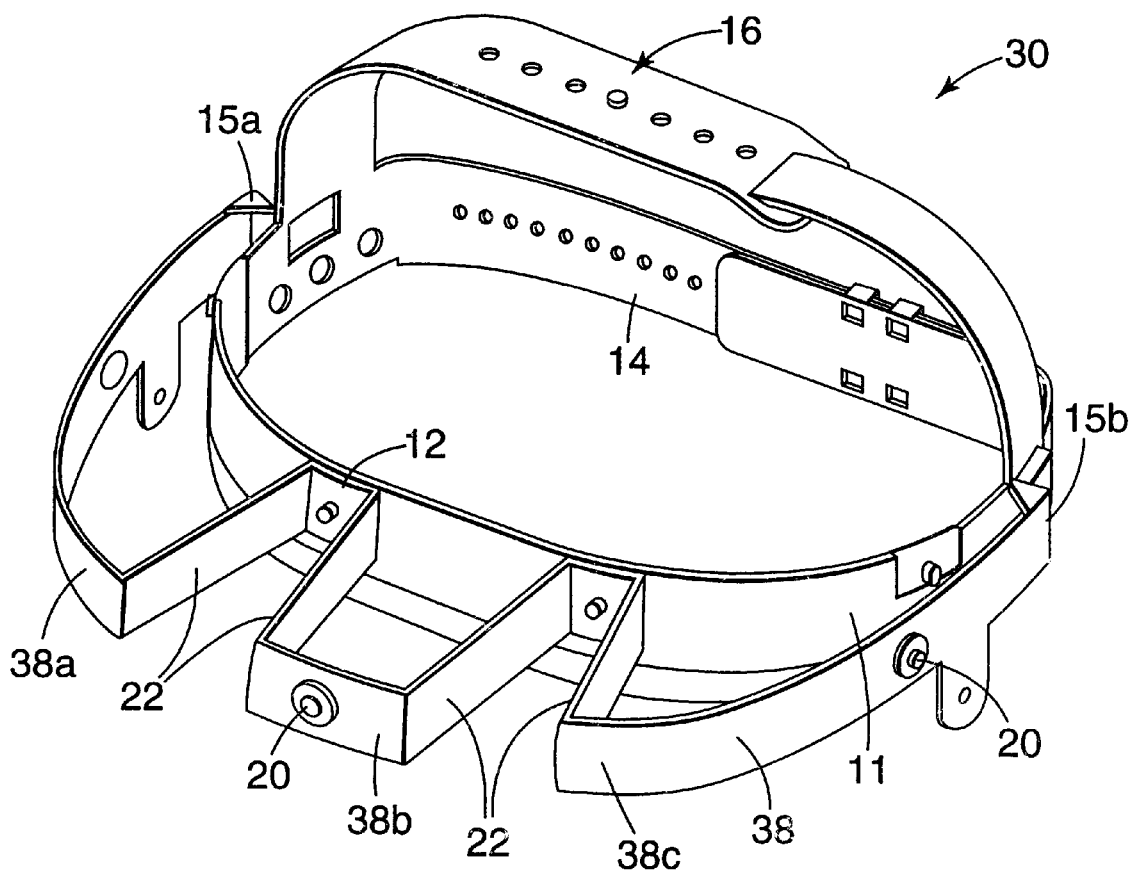
FIG. 3 is a perspective view of a hood head suspension 30 in accordance with a second embodiment of the present invention.

Braces 22 attach lens mount 18 to headband 11 to provide increased lateral (side-to-side) stability. Braces 22 may be referred to as arms, straps, posts or other such structures. Examples of designs and configurations for braces 22 are depicted in FIGS. 1 and 3. It should be understood that mounting points 15a and 15b may contribute to the stability of lens mount 18 depending on the placement and positioning of points 15a and 15b, however mounting points 15a, 15b are primarily intended for connection of lens mount 18 to headband 11.

Figure 2:
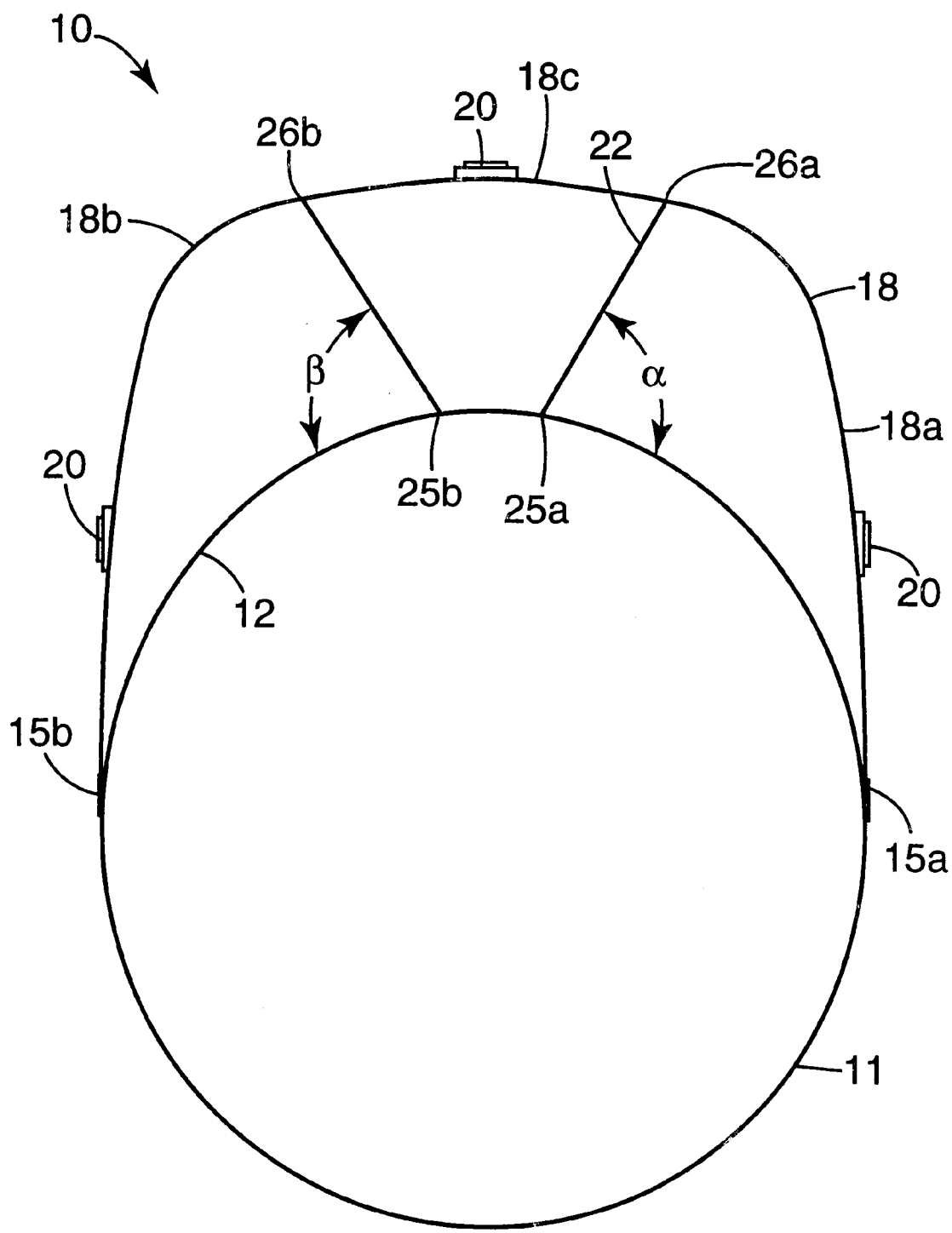
FIG. 2 is a top view of the hood head suspension 10 shown in FIG. 1 without crown strap 16.

A preferred embodiment for a head suspension 10 according to the present invention is shown in FIGS. 1 and 2. FIGS. 1 and 2 show two braces 22 symmetrically spaced near the middle of lens mount 18. Braces 22 extend from headband 11 and diverge to lens mount 18. Braces 22 are connected to headband 11 at points 25a, 25b and to lens mount 18 at points 26a, 26b as shown in FIG. 2. Braces 22 are nonparallel to one another and extend from headband 11 at angles $\alpha$ and $\beta$. Braces 22 are generally about 2 to 10 cm long and can have a distance of approximately 5 to 15 cm between the two.

It is preferred that the braces be non-parallel in positioning with respect to each other. The braces 22 create pivot points on the headband 11 and lens mount 18 as depicted for example in FIG. 2 at 25a, 26a and 25b, 26b. If the pivot point is not stabilized, a force exerted at one or more of these points may tend to cause the lens mount 18 to collapse towards the wearer's face. However, the non-parallel positioning acts to stabilize the pivot points, thereby reducing the tendency of lens mount 18 and the attached lens to move or be displaced. Most preferably, the braces 22 diverge from each other because it is believed this positioning provides the greatest degree of Stabilization.

It may be preferable to position braces 22 so that angles $\alpha$ and $\beta$ are between about 30 to 60 degrees, more preferably about 45 degrees. To provide even support for lens mount 18, angles $\alpha$ and $\beta$ should be the same. Preferably, neither angle $\alpha$ nor $\beta$ extends directly out from headband 11, thereby creating an angle of 90°. Embodiments where angles $\alpha$ and $\beta$ are greater than 90°, that is, where braces 22 converge as they extend from headband 11 to lens mount 18, may also provide additional stability to the face shield in respect to the wearer's shoulders and shroud.

Braces 22 may have any thickness, length and width, so long as the braces do not fully block the flow of air from the top of the head down between the plastic lens and the wearer's face. Preferably, brace 22 is between about 2 and 10 cm in length, and is about 2 cm wide, although other dimensions can be used.

It is foreseen that other designs, for example three braces, four braces, etc. would also work as long as there are at least two braces that are nonparallel. Preferably, multiple braces are symmetrically spaced around the center of the lens mount to provide even stabilization. If multiple braces 22 are used, it is not necessary that they are identical in, for example, shape or size.

In another embodiment, shown in FIG. 3, head suspension 30 has headband 11 comprising forehead strap 12, back strap 14, and crown strap 16, such as in the embodiment shown in FIG. 1. Head suspension 30 further comprises lens mount 38, having three sections, 38a, 38b, and 38c. The center section 38b is attached to forehead strap 12 by two braces 22, one at each end of section 38b. The outer lens mount sections 38a, 38c are each attached to forehead strap 12 by a brace 22 at one end and a mounting point 15a, 15b, respectively, at the other end. Multiple braces 22 may be positioned at an angle to each another or may be parallel, however all braces 22 should not be parallel to each other.

Braces 22 may initially be separate pieces. Braces 22 are then attached to the lens mount 18 and to the headband 11 to provide increased stability for the lens mount. The attachment can be secured by mechanical means such as clips, hooks, insertion into a slot, or hook and loop, by adhesive, or by other attachment methods such as ultrasonic or thermal welding.

To decrease the cost of the head suspension 10, braces 22 may be integral with a part of headband 11. For example, slits or cuts can be made in headband 11 so that braces 22 can be folded out from headband 11 and attached to lens mount 18. Braces 22 are made from a portion of headband 11. An example of such an embodiment is shown in FIG. 1. In another version, braces 22 can be integrally molded with headband 11 so that braces 22 extend out from headband 11 without a portion of headband 11 being used.

Alternatively, braces 22 may be integral with the lens mount 18. For example, the lens mount 18 can be converted (i.e., slit, cut, etc.) so that braces 22 can be folded out from the material of the lens mount and attached to headband 11. Braces 22 would be made from a portion of the lens mount. In another version, braces 22 can be integrally molded with the lens mount. Braces 22 could extend out from a continuous lens mount or could be integral with a discontinuous lens mount such as lens mount 38 in FIG. 3.

Both head suspension 10 and 30, and any other embodiments, should be flexible to easily conform to the wearer's head and should be light and comfortable. Head suspension 10, 30 is preferably manufactured from plastic, such as a thermoplastic, a thermoset, or an elastomeric material. Thermoplastic material is the most preferred. Preferably, headband 11, lens mount 18, 38 and braces 22 are manufactured from the same material, although in some embodiments it may be desirable to utilize a variety of materials.

Head suspension 10, 30 can be manufactured by molding, preferably by injection molding. For example, the embodiment shown in FIG. 1 could be made by injection molding two pieces and then assembling. The first piece would be the crown strap 16, and the second piece would be the headband 11, including back strap 14, and forehead strap 12. Braces 22 could be molded integral with forehead strap 12 and then bent outward to provide the extending arms at angles α and β. The second piece would be lens mount 18 with snaps 20. The two pieces can be attached together by any methods such as mechanical systems or adhesive. Similarly, the embodiment shown in FIG. 3 could be molded as two pieces, except however, braces 22 would be molded integral with lens mount 38. Lens mount 38 and braces 22 can attach to forehead strap 12 by passing a protrusion through a hole in forehead strap 12.

In another variation, head suspension 10, 30 may be manufactured from a single piece of material that is converted (stamped, die cut, slit, etc.) to a shape that can then be folded to the desired final shape. In such a manufacturing method, headband 11, lens mount 18, braces 22, and optional crown strap 16 are converted from a single piece of material. In yet another embodiment, head suspension 10 may be constructed of multiple individual parts that are assembled.

Various optional features may be included in head suspension 10 to increase the wearer's comfort, to improve worker conditions, and to provide a secure fit of the head suspension onto the wearer's head. For example, headband 11 and any crown strap 16 may be padded to provide a more comfortable and conformable fit. Low-density foam is a preferred material. Headband 11, in particular forehead strap 12, may include an absorbent material, for example terry cloth or other 'sweatband' type material to absorb perspiration. It may be preferable that the absorbent material is easily removable and replaceable throughout the useful life of the headband 11.

In order for the improved head suspension to optimally stabilize the lens, the head suspension should securely fit onto the wearer's head. The head suspension should not rotate, slide, or otherwise undesirably move in relation to the head. An adjustable headband and crown improves the secureness of the fit. In some head suspensions where a ratcheting rear adjustment is used for the headband, the ratcheting mechanism and its straps may be positioned below the headband, thereby providing another strap to increase the secureness of the suspension onto the head.

In addition to increasing comfort, foam padding can conform the head suspension to the wearer's head. The compressible foam is typically able to compensate for extra space between the headband and the wearer's head. A chinstrap can be added to the head suspension to improve the stability on the wearer's head.

The foregoing description, which has been disclosed by way of the above discussion, addresses embodiments of the present invention encompassing the principles of the present invention. The embodiments may be changed, modified and/or implemented using various types of arrangements. Those skilled in the art will readily recognize various modifications and changes which may be made to the present invention without strictly following the exemplary embodiments and applications illustrated and described herein, and without departing from the scope of the present invention which is set forth in the following claims.

What is claimed is:

1. A head suspension for use with a hood and for suspending a lens therefrom, the head suspension comprising:
   a headband;
   a lens mount extending from the headband for mounting the lens to the head suspension, the lens mount having two ends each of which is attached to the headband at a mounting point, wherein the lens mount is further attached to the headband at least two additional points between the mounting points by nonparallel braces that provide increased lateral stability to the lens mount.

2. The head suspension according to claim 1 wherein the headband comprises a forehead strap and a back strap.

3. The head suspension according to claim 1 wherein the head suspension further comprises a crown strap.

4. The head suspension according to claim 1 wherein the crown strap is adjustable.

5. The head suspension according to claim 1 comprising two braces that diverge as they extend from the headband.

6. The head suspension according to claim 5 wherein the two braces are symmetrically spaced about the center of the lens mount.

7. The head suspension according to claim 1 wherein the braces are integral with the lens mount.

8. The head suspension according to claim 1 wherein the braces are integral with the headband.

9. The head suspension according to claim 1 wherein the lens mount comprises one piece.

10. The head suspension according to claim 1 wherein the lens mount comprises several sections.

11. The head suspension according to claim 10 wherein each section is attached to the headband by at least one brace.

12. The head suspension according to claim 1 wherein the lens is attached to the lens mount via snaps.

13. The head suspension according to claim 1 wherein the head suspension material is thermoplastic.

14. The head suspension according to claim 1 wherein the headband is adjustable.

15. The head suspension according to claim 1 further comprising padding on the headband.

16. A head suspension for use with a hood and for suspending a lens therefrom, the head suspension comprising:

a headband, a lens mount for mounting the lens to the head suspension, the lens mount having two ends and the lens mount attached to the headband at the two ends, wherein the lens mount is discontinuous;

at least two nonparallel braces extending between the headband and the lens mount at least two points between the two ends of the lens mount to provide increased lateral stability for the lens mount, wherein the braces are integral with either the headband or the lens mount and the braces are attached to headband and lens mount.

17. The head suspension according to claim 16 wherein the lens mount has two sections.

* * * * *

UNITED STATES PATENT AND TRADEMARK OFFICE
CERTIFICATE OF CORRECTION

PATENT NO.    : 6,367,085 B1
DATED         : April 9, 2002
INVENTOR(S)   : Berg, Richard C.

It is certified that error appears in the above-identified patent and that said Letters Patent is hereby corrected as shown below:

Column 1,
Line 25, delete "QCr$^{TM}$" and insert in place thereof -- QC$^{TM}$ --.

Column 2,
Line 49, delete "M" and insert in place thereof -- 3M --.

Column 3,
Line 65, delete the "." after "18" and insert in place thereof -- , --.
Line 65, delete "The" and insert in place thereof -- the --.

Column 4,
Line 38, delete "Stabilization" and insert in place thereof -- stabilization --.

Signed and Sealed this

Fifteenth Day of October, 2002

*Attest:*

JAMES E. ROGAN
*Attesting Officer*    *Director of the United States Patent and Trademark Office*